(12) United States Patent
Overaker et al.

(10) Patent No.: US 6,391,046 B1
(45) Date of Patent: May 21, 2002

(54) OMNI-ACTUATABLE HAND-HELD SURGICAL INSTRUMENTS

(75) Inventors: Ronald F. Overaker; Brian C. Dodge, both of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/549,469

(22) Filed: Apr. 14, 2000

(51) Int. Cl.⁷ .............................................. A61B 17/00
(52) U.S. Cl. ...................... 606/205; 606/174; 81/177.1
(58) Field of Search ........................... 606/1, 170, 167, 606/171, 205, 206, 210, 127, 51, 52, 174; 30/137; 294/99.2, 115; 600/562–567; 81/177.1, 489

(56) References Cited

U.S. PATENT DOCUMENTS

| | | |
|---|---|---|
| 4,760,848 A | 8/1988 | Hasson |
| 5,211,652 A | 5/1993 | Derbyshire |
| 5,275,607 A | 1/1994 | Lo et al. |
| 5,290,302 A | 3/1994 | Pericic |
| 5,338,317 A | 8/1994 | Hasson et al. |
| 5,634,918 A | 6/1997 | Richards |
| 5,827,291 A | 10/1998 | Fucci et al. |
| 5,830,231 A | 11/1998 | Geiges, Jr. |
| 5,908,426 A | 6/1999 | Pierce |
| 5,984,685 A | 11/1999 | Farley et al. |

FOREIGN PATENT DOCUMENTS

| | | | |
|---|---|---|---|
| DE | 3526821 A | * | 2/1985 |
| GB | 2 091 624 A | | 8/1982 |

* cited by examiner

*Primary Examiner*—Michael J. Milano
*Assistant Examiner*—William W Lewis
(74) *Attorney, Agent, or Firm*—Nixon & Vanderhye P.C.

(57) ABSTRACT

Hand-held instruments which may be employed to actuate a distally mounted tool by application of radial compressive force about the instrument circumference (i.e., omni-actuatable). In preferred forms, hand-held instruments have a handle which includes an actuator assembly for actuating a tool, wherein the actuator assembly has a generally V-shaped circumferential channel in which an actuator band is seated. A slide ring assembly is provided which defines the generally V-shaped circumferential channel and has at least one slide ring mounted for longitudinal movements relative to the handle. The actuator band is radially flexible. Thus, in response to a compressive force, the actuator band seated within the generally V-shaped channel will be flexed radially inwardly to thereby moves the slide ring longitudinally. The slide ring, in turn, coacts operatively with the distally mounted tool (e.g., through a longitudinally slidable actuator pin). Radial motion of the actuator band is thereby translated into longitudinal motion of the slide ring, which longitudinal motion is then employed to actuate the tool.

35 Claims, 5 Drawing Sheets

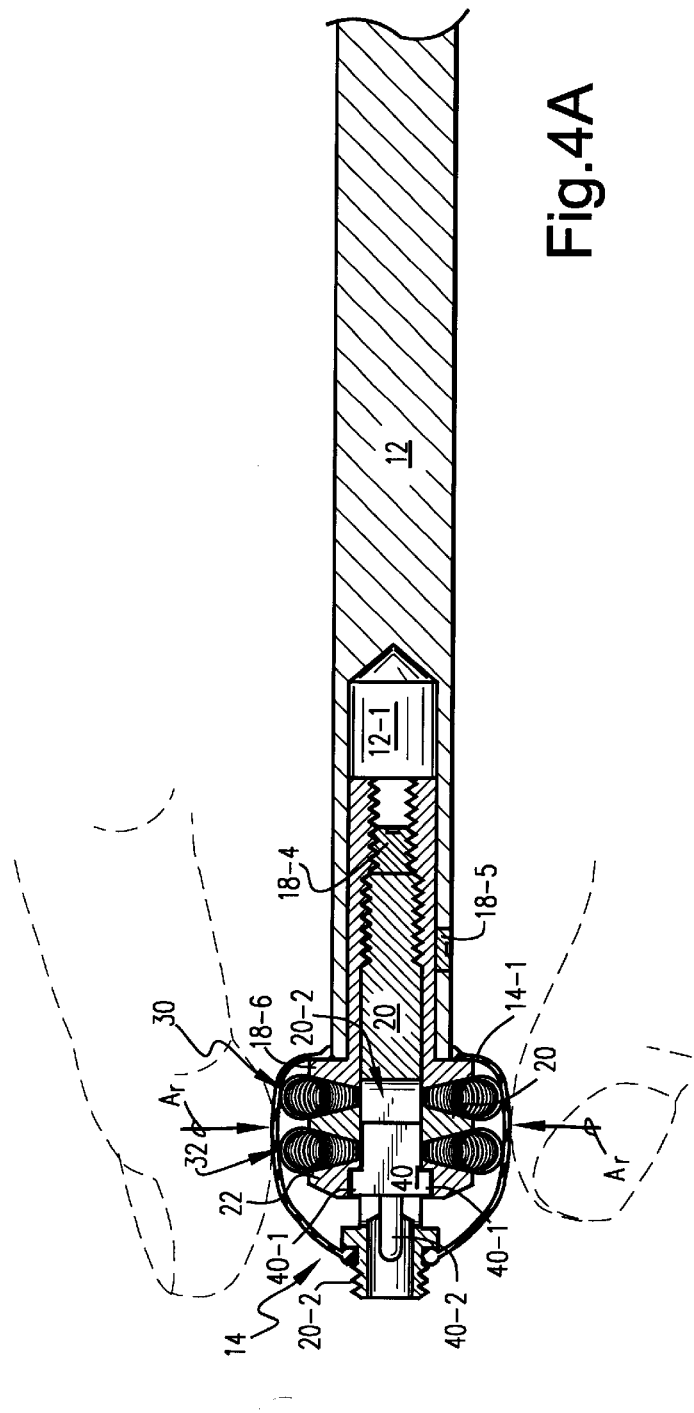
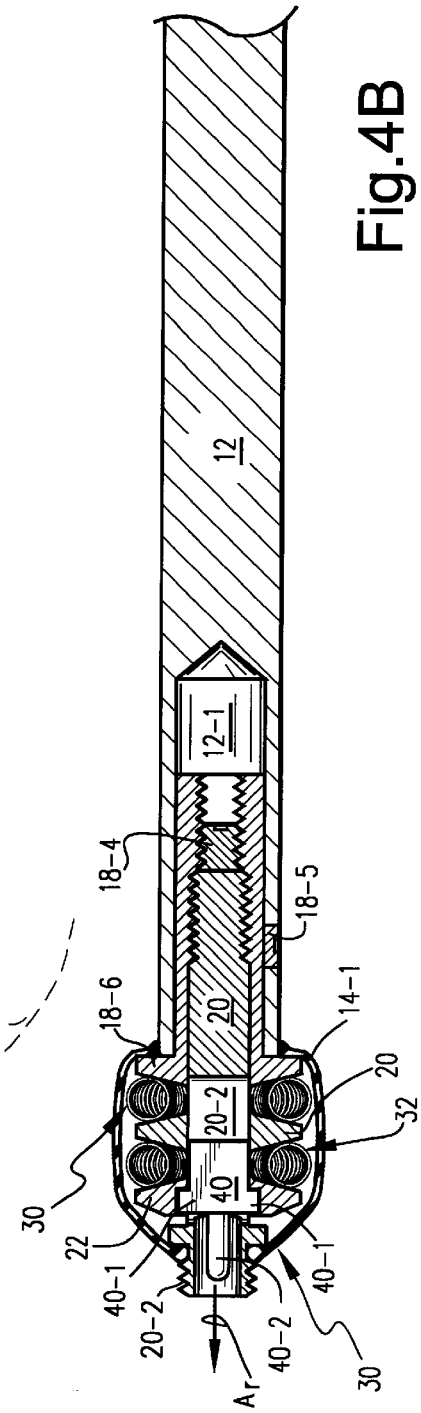

US 6,391,046 B1

OMNI-ACTUATABLE HAND-HELD SURGICAL INSTRUMENTS

FIELD OF THE INVENTION

The present invention relates generally to hand-held instruments and tools. In preferred forms, the present invention relates to hand-held surgical instruments, especially those usefully employed for ophthalmic surgical procedures.

BACKGROUND OF THE INVENTION

Ophthalmic surgical procedures require the use of miniaturized instruments such as, for example, forceps, scissors and the like in order to allow the surgeon to operate on and within a patient's eye. One well known instrument that is used for such ophthalmic surgical procedures is the so-called Sutherland-type instrument commercially available from Grieshaber & Co., Inc. The Sutherland-type instrument has a pen-like handle and uses a lever as an actuator for actuating mechanically operable spring-loaded tools, such as forceps, scissors, knives and the like which are threaded or otherwise operably connected to the distal end of the handle.

Recently, improvements to such Sutherland-type instruments have been proposed in U.S. Pat. No. 5,634,918 (the entire content of which is expressly incorporated hereinto by reference). In general, the improvements proposed by the '918 Patent include providing a circumferentially arranged series of lever-like triggers which are pivotal in response to a radial force being applied thereto. Radially inward and outward pivotal movements of one trigger will, in turn, be converted respectively into rightward and leftward translation of the trigger retainer and is accompanied by like simultaneous movement of all the other triggers. Thus, any working tool attached operable to the trigger retainer will likewise translate rightward and leftward therewith.

SUMMARY OF THE INVENTION

The present invention is directed to further improvements in surgical instruments of the Sutherland-type. In this regard, the present invention broadly is directed to hand-held instruments which may be employed to actuate a distally mounted tool by application of radial force about the instrument circumference (i.e., omni-actuatable). In preferred forms, the present invention is embodied in hand-held instruments having a handle which includes an actuator assembly for actuating a tool, wherein the actuator assembly has a generally V-shaped circumferential channel in which an actuator band is seated. A slide ring assembly is provided which defines the generally V-shaped circumferential channel and has at least one slide ring mounted for longitudinal movements relative to the handle.

The actuator band is radially flexible. Thus, in response to compressive force, the actuator band seated within the generally V-shaped channel will be flexed radially inwardly to thereby move the slide ring longitudinally. The slide ring, in turn, coacts operatively with the distally mounted tool (e.g., through a longitudinally slidable actuator pin). Radial motion of the actuator band is thereby translated into longitudinal motion of the slide ring, which longitudinal motion is then employed to actuate the tool.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIGS. 4A and 4B are each longitudinal cross-sectional elevational views showing the operation of the surgical instrument in accordance with the present invention.

DETAILED DESCRIPTION OF THE INVENTION

Figure 1:
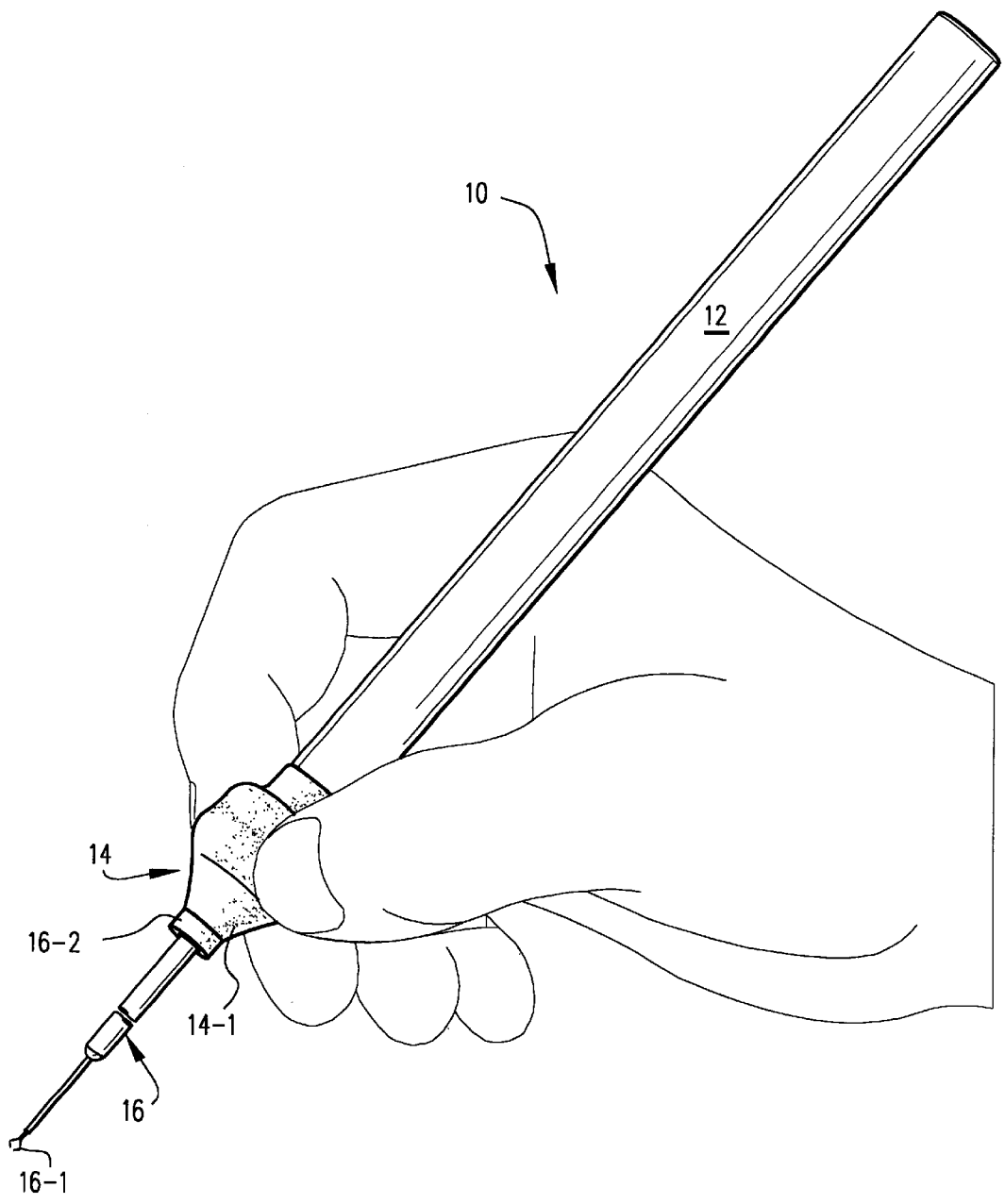
FIG. 1 is a perspective view of one embodiment of a hand-held surgical instrument according to the present invention.

Accompanying FIG. 1 depicts one exemplary embodiment of a hand-held surgical instrument 10 according to the present invention. In this regard, the surgical instrument 10 includes an elongated handle 12 sized and configured to allow the instrument 10 to be handled manually by a surgeon during surgical procedures. The handle 12 includes a manually operated actuator assembly 14 which serves to actuate a tool 16 operatively attached to, and extending from, the distal end of the handle. The tool 16, for example, may be a miniature forceps 16-1 positioned at the distal-most end thereof which open and close in response to actuation of the actuator assembly 16 in a manner that will be described in greater detail below. The component parts of the actuator assembly 14 are covered by a resilient elastomeric boot 14-1.

Figure 2:
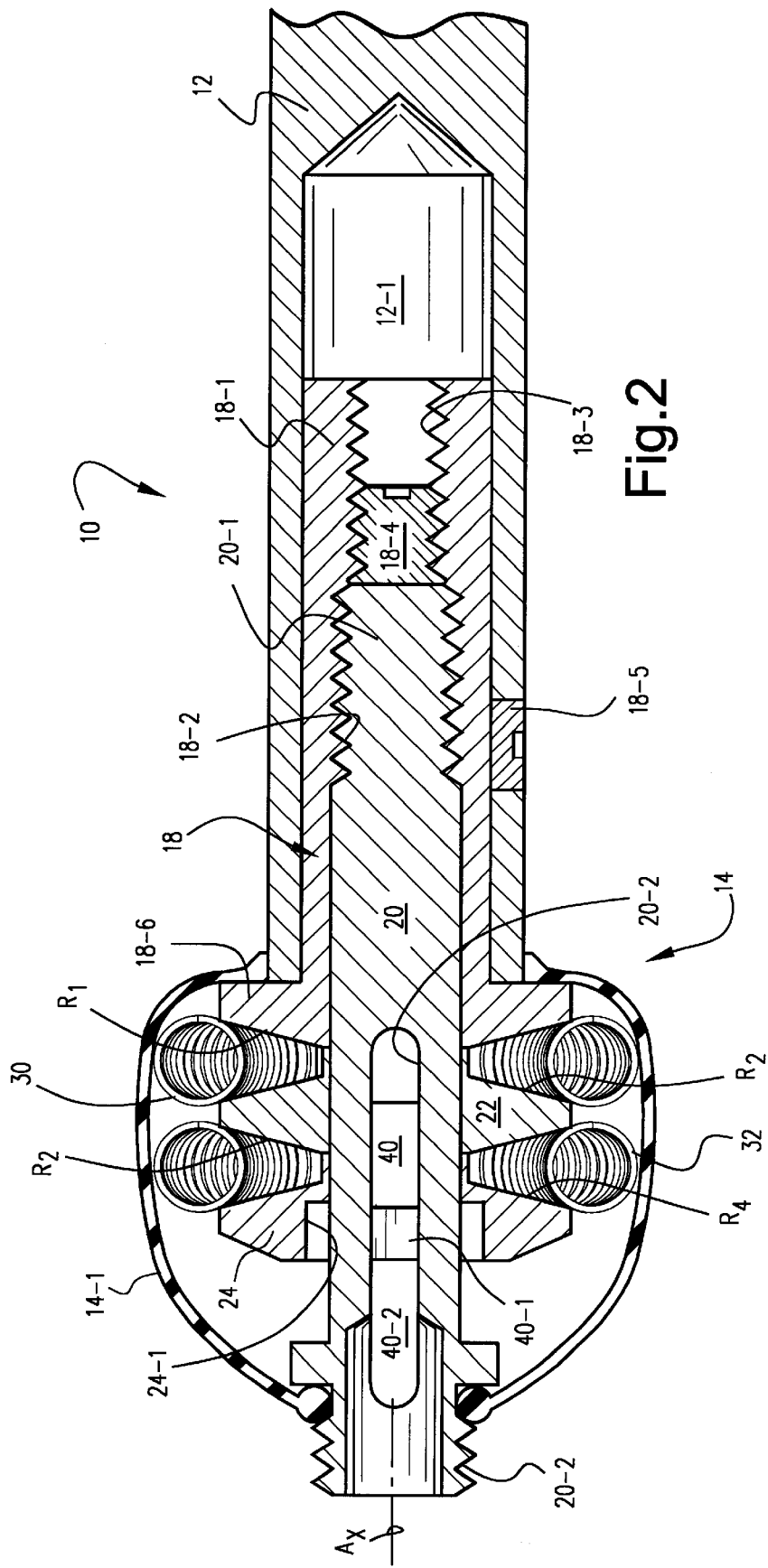
FIG. 2 is an enlarged cross-sectional view of the actuator assembly employed in the surgical instrument of the present invention.
Figure 3:
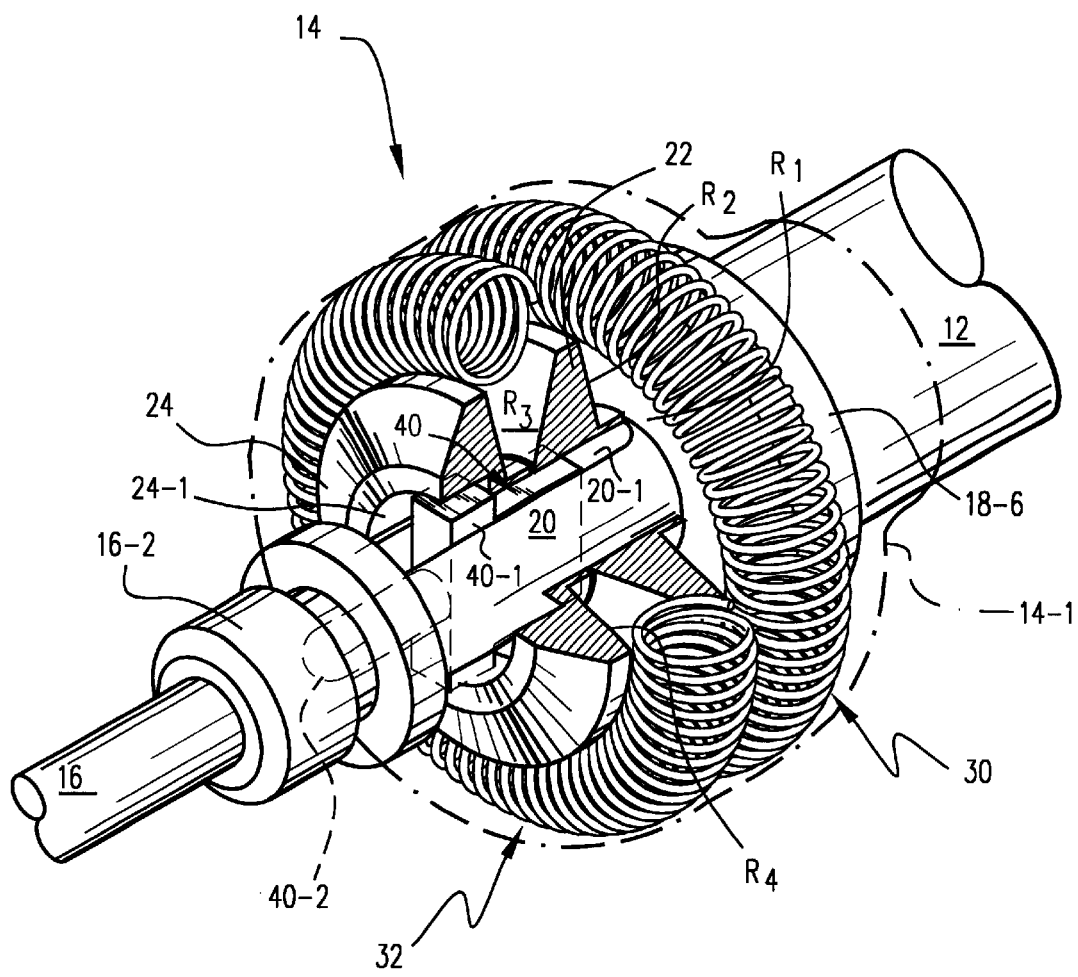
FIG. 3 is an enlarged perspective view, partly in section, of the actuator assembly depicted in FIG. 2.

As is perhaps more clearly shown in FIGS. 2 and 3, the distal end of the handle 12 is provided with a cylindrical recess 12-1 which is adapted to receive a conformably shaped proximal end 18-1 of the core housing 18. The proximal end 18-1 is provided with an internally threaded bore comprised of a coaxially aligned series of opposite-hand thread sections 18-2, 18-3. The distal thread section 18-2 threadably receives the threaded proximal end 20-1 of the cylindrical core member 20. The proximal thread section 18-3 receives a set screw 18-4 which positionally locks the core member 20 relative to the core housing 18. The core housing 18, in turn, is positionally locked within the recess 12-1, and hence to the handle 12, via set screw 18-5.

The distal end of the core housing 18 integrally includes a fixed-position annular actuation flange 18-6 whose forward face defines a ramp surface R1. A pair of slide rings 22, 24 are sleeved over the cylindrical outer surface of the core member 20 so as to be capable of slidable reciprocal rectilinear movements along the elongate axis ($A_x$, in FIG. 2) of the instrument 10. The ramp member 22 defines a pair of ramp surfaces R2, R3 while the ramp member 24 defines a ramp surface R4. As can be seen in FIG. 2, the ramp surfaces R1 and R2 oppose one another while the ramp surfaces R3 and R4 are in opposition to one another. Thus, each of the opposed ramp surface pairs R1, R2 and R3, R4 respectively define a generally V-shaped channel which receives an endless, radially flexible actuator band 30, 32.

Each of the ramp surfaces R1–R4 is most preferably non-linear. That is, each of the ramp surfaces R1–R4 is most preferably a convexly arcuate surface of a radius which is sized to intersect the hypotenuse of a right triangle whose base aligned with the axis $A_x$ has the distance needed for reciprocal displacement ("throw") to operate the tool 14.

The non-linear ramp surfaces R1–R4 thus create tangential surface-to-surface contact with the external cross-sectionally circular surfaces of the actuating bands 30, 32. This tangential contact between the ramp surfaces R1–R4 and the actuating bands allows for a smooth transition from the initial break-away activation force (i.e., the minimum radial force needed to be exerted on the actuating bands 30, 32 which causes responsive axial movement of the slide rings 30, 32). Once the initial brake-away activation force has been exceeded, the tangential contact between the actuating bands and the ramp surfaces R1–R4 allows for an ever decreasing force requirement to be exerted in order to achieve axial movements of the slide rings 30, 32. In other words, for a given throw to operate the tool 16, the non-linear ramp surfaces R1–R4 ensure that the manual actuation force which is exerted against the bands 30, 32 decreases as the maximum throw or axial displacement of the tool 16 is approached.

The ramp surfaces R1–R4 and the actuating bands 30, 32 should be formed of materials which minimize frictional resistance, for example, polished stainless steel. The external surfaces of the bands 30, 32 may also coated with a low-friction material (e.g., PTFE). If desired, however, the ramp surfaces R1–R4 could be linear, in which case, the decrease in actuation force noted above would not be an important design feature for the particular instrument in which such surfaces were embodied.

The core member 20 defines a lengthwise slot 20-2 in which an actuator pin 40 is positioned. The actuator pin 40 includes a pair of diametrically opposed, outwardly projecting tabs 40-1 which are seated within the annular recess 24-1 defined in the moveable ramp member 24 (see FIG. 2). An actuation tip 40-2 projects distally from the pin 40 so as to coact with the actuation mechanism (not shown) associated with the tool 16.

The distal end 20-3 of the core member 20 is threaded so as to allow the actuation mechanism 16-2 of the tool 16 to be removably threadably attached thereto. It is to be understood, of course, that a variety of tools may be employed in operative union with the handle 12 and actuator assembly 14 of this invention, i.e., so a single handle can hold one of a number of interchangeable tools as may be desired by the surgeon. The actuation mechanism 16-2 of the tool 16 will therefore operatively present itself to the tip 40-2 of pin 40 to allow actuation in response to operation of the actuation assembly 14. In this regard, the actuation mechanism 16-2 of the tool 16 will include a bias spring (not shown) that forces the pin 40 to its inactive, proximal position within the slot 20-2 of core member 20. Such a state is shown in FIG. 4A.

When the surgeon desires to actuate the tool 14, a compressive force (arrows Ar in FIG. 4A) is manually applied against the actuator bands 30, 32 through the boot 14-1 of actuator assembly 14. The actuator bands 30, 32 are thus flexibly radially depressed within the generally V-shaped channels defined between the opposing ramp surfaces R1, R2 and R3, R4, respectively, thereby slidably driving the ramp members 22, 24 in a distal direction along the longitudinal axis $A_x$ of the instrument 10 (i.e., in the direction of arrow Al in FIG. 4B).

The ramp member 24 in turn pushes against the tabs 40-1 of the actuator pin 40 thereby responsively causing the actuator tip 40-2 to be displaced longitudinally between its retracted position shown in FIG. 4A and into its extended position shown in FIG. 4B. The distance which the actuator tip 40-2 moves between such retracted and extended positions is the "throw" needed to operate the tool 16. That is, as explained previously, the tool 16 is, in and of itself conventional and includes a spring biased activation mechanism 16-2 which is engaged by the tip 40-2 to thereby, in turn, activate the tool 16. In the case of the example depicted in FIG. 1, the miniature forceps 16-1 are caused to close in response to the actuator bands 30, 32 being radially depressed.

Various modifications and equivalent structures may be envisioned for the instrument 10 according to the present invention. For example, the actuator bands 30, 32 have been depicted as being in the form of endless torroidally wound tension springs. However, other forms of springs or radially-collapsible structures may be envisioned. Thus, elastomeric bands may be employed provided they are coated or otherwise have a relatively low friction surface in contact with the ramp surfaces R2–R4 for the reasons as previously noted.

Figure 5:
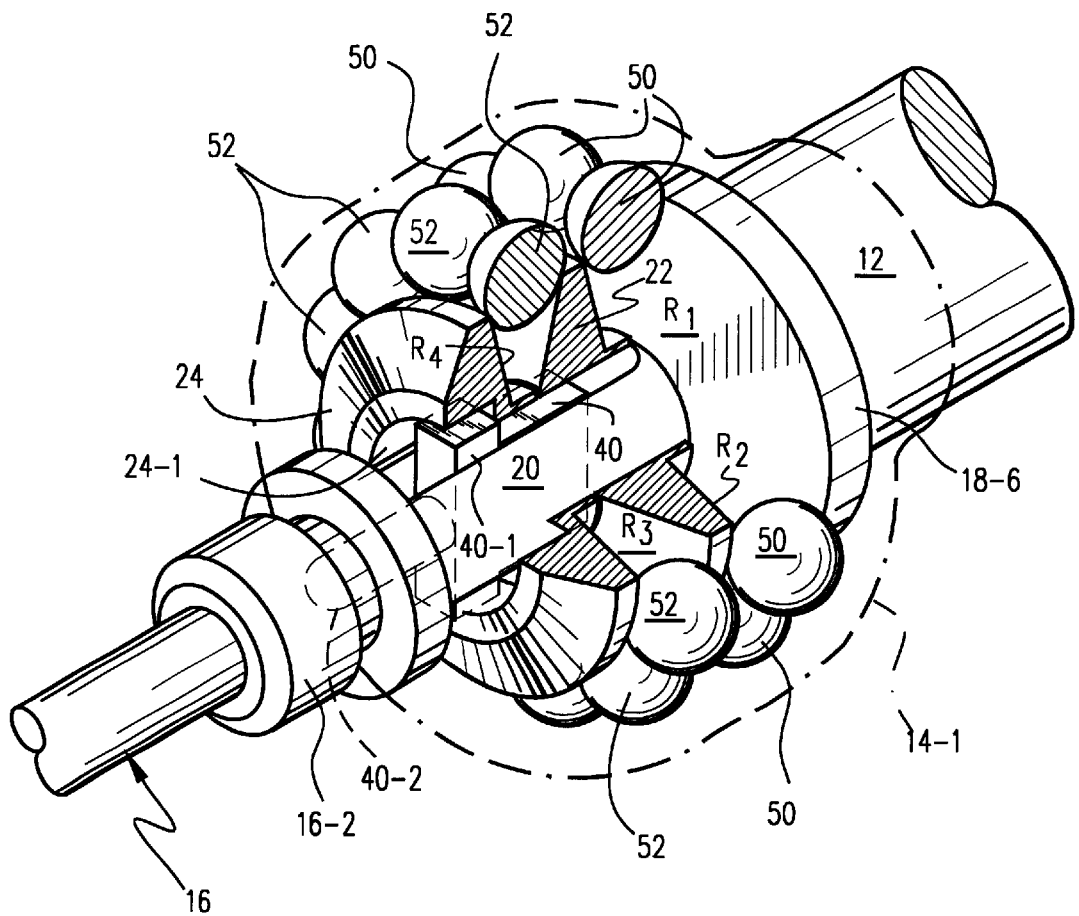
FIG. 5 is an enlarged perspective view, partly in section, of another embodiment of an actuator assembly that may be employed in the surgical instruments of the present invention.

Furthermore, as shown in FIG. 5, the actuator bands may be in the form of a circumferentially arranged series of spherical bearings (a few of which are identified in FIG. 5 by reference numerals 50 and 52) which are seated respectively within the generally V-shaped channels defined between opposed ramp surfaces R1, R2 and R3, R4. These bearings 50, 52 may be detached from one another as shown in FIG. 5, or alternatively may be flexibly attached to one another as might be present in a ball chain or like structures. As was the case with the actuator bands 30, 32 discussed above, the circumferential arrangement of the spherical bearings 50, 52 allows for them to be radially depressed within the generally V-shaped channels defined between opposed ramp surfaces R1, R2 and R3, R4 so as to activate the tool 14 carried at the distal end of the handle 12.

A pair of slide rings 20, 22 has also been depicted with a corresponding pair of actuator bands as this represents a presently preferred form of the invention. However, more or fewer such slide rings and actuator bands may be provided without departing from the scope of the present invention. Thus, a single slide ring and a single actuator band is contemplated by the present invention.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A hand-held instrument having a handle which includes an actuator assembly for actuating a tool, said actuator assembly comprising:

a slide ring assembly which defines a generally V-shaped circumferential channel and having at least one slide ring mounted for longitudinal movements relative to the handle; and a radially flexible actuator band seated within said generally V-shaped channel, wherein radial force applied to said actuator band causes said actuator band to be radially depressed within said generally V-shaped channel to thereby responsively move said at least one slide ring longitudinally relative to the handle.

2. The instrument of claim 1, wherein said actuator band includes an arcuate surface in contact with said V-shaped channel.

3. The instrument of claim 2, wherein said actuator band includes an endless spring.

4. The instrument of claim 2, wherein said actuator band includes a circumferentially disposed series of spherical bearings.

5. The instrument of claim 1, wherein said slide ring assembly includes opposed ramp surfaces which define said V-shaped channel.

6. The instrument of claim 5, wherein said ramp surfaces are convexly arcuate.

7. The instrument of claim 5, wherein said ramp surfaces are non-linear.

8. The instrument of claim 1, wherein said actuator assembly includes a core member having a lengthwise slot and an actuator pin slidably received within said slot, wherein said at least one slide ring is in operative contact with said actuator pin such that said at least one slide ring and said actuator pin longitudinally move in response to said radial force applied to said actuator band.

9. The instrument of claim 8, wherein said actuator pin has a radially extending tab, and wherein said at least one slide ring has an annular recess which receives said tab.

10. The instrument of claim 8, wherein said actuator pin has a tip which extends longitudinally outwardly from said pin.

11. The instrument of claim 1, wherein said slide ring assembly includes a fixed-position actuator flange in opposition to said at least one slide ring, and wherein said V-shaped channel is defined between said actuator flange and said at least one slide ring.

12. The instrument of claim 11, wherein said actuator assembly includes a core housing attached to said handle, and wherein said actuator flange is integral with said core housing at a distal end thereof.

13. The instrument of claim 12, wherein said actuator assembly includes a core member coupled to said core housing, said core member having a lengthwise slot and an actuator pin slidably received within said slot, wherein said at least one slide ring is in operative contact with said actuator pin such that said at least one slide ring and said actuator pin longitudinally move in response to said radial force applied to said actuator band.

14. The instrument of claim 13, wherein said actuator pin has a radially extending tab, and wherein said at least one slide ring has an annular recess which receives said tab.

15. The instrument of claim 13, wherein said actuator pin has a tip which extends longitudinally outwardly from said pin.

16. The instrument of claim 12, wherein said core housing includes an internally threaded bore, and wherein said core member includes a threaded proximal end which is threadably coupled to said threaded bore of said core housing.

17. The instrument of claim 16, further comprising a set screw threadably received in said threaded bore in opposition to said threaded proximal end of said core member to positionally fix said core member relative to said core housing.

18. A hand-held instrument having a handle which includes actuator means for translating radial forces applied thereto into longitudinal movements of a distally mounted tool element, said actuator means comprising:

coaxially opposed first and second rings, said first ring having a fixed-position and said second ring being longitudinally moveable relative to said first ring, wherein said first and second rings have respective converging ramp surfaces to define a generally V-shaped channel therebetween; and an actuator band seated in said channel and having a cross-sectionally arcuate exterior surface in contact with said ramp surfaces, wherein said radial forces applied to said actuator band causes said actuator band to be radially depressed within said channel and thereby responsively move said second ring longitudinally relative to said first ring.

19. The instrument of claim 18, further comprising a longitudinally moveable third ring coaxially opposed to said second ring, said second and third rings having converging ramp surfaces to define a generally V-shaped second channel therebetween, and a second actuator band seated in said second channel and having a cross-sectionally arcuate exterior surface in contact with said ramp surfaces of said second and third rings.

20. The instrument of claim 18, wherein said actuator band is an endless spring.

21. The instrument of claim 18, wherein said actuator band is a circumferentially disposed series of spherical bearings.

22. The combination comprising a surgical tool, and an instrument as in claim 1 or 18.

23. A hand-held surgical instrument having a handle which includes a actuator assembly, and a surgical tool attached to a distal end of said handle and being operable in response to application of radial force to said actuator assembly, wherein said actuator assembly comprises:

a first fixed-position ring;

a second longitudinally moveable ring in coaxial opposition to said first ring;

said first and second rings having respective annular ramp surfaces which define therebetween a generally V-shaped channel in cross-section;

an actuator band seated in said channel, said actuator band being radially depressed within said channel in response to a radial force applied thereto so as to responsively longitudinally move said second ring relative to said first ring and thereby actuate said surgical tool.

24. The instrument of claim 23, wherein said actuator band includes an arcuate surface in contact with said V-shaped channel.

25. The instrument of claim 24, wherein said actuator band is an endless spring.

26. The instrument of claim 24, wherein said actuator band is a circumferentially disposed series of spherical bearings.

27. The instrument of claim 23, wherein said ramp surfaces are convexly arcuate.

28. The instrument of claim 23, wherein said ramp surfaces are non-linear.

29. The instrument of claim 23, wherein said actuator assembly includes a core member having a lengthwise slot and an actuator pin slidably received within said slot, wherein said second ring is in operative contact with said actuator pin such that said second ring and said actuator pin longitudinally move in response to said radial force applied to said actuator band.

30. The instrument of claim 29, wherein said actuator pin has a radially extending tab, and wherein said second ring has an annular recess which receives said tab.

31. The instrument of claim 30 wherein said actuator pin has a tip which extends longitudinally outwardly from said pin to actuate said surgical tool.

32. The instrument of claim 28, wherein said actuator assembly includes a core housing fixed to said handle, wherein said core member is fixed to said core housing.

33. The instrument of claim 32, wherein said first ring is formed integrally at a distal end of said core housing.

34. The instrument of claim 33, wherein said core member and said core housing are threadably coupled to one another.

35. The instrument of claim 23, further comprising a longitudinally moveable third ring coaxially opposed to said second ring, said second and third rings having converging ramp surfaces to define a generally V-shaped second channel therebetween, and a second actuator band seated in said second channel and having a cross-sectionally arcuate exterior surface in contact with said ramp surfaces of said second and third rings.

* * * * *